(12) United States Patent
Marikkar et al.

(10) Patent No.: US 10,743,592 B2
(45) Date of Patent: Aug. 18, 2020

(54) SMART APPAREL

(71) Applicant: MAS INNOVATION (PVT) LIMITED, Colombo (LK)

(72) Inventors: Fatima Ilma Marikkar, Colombo (LK); Alujjage Don Vishwa Aluthge, Colombo (LK); Vivek Vashdev Ramchandani, Colombo (LK)

(73) Assignee: MAS INNOVATION (PVT) LIMITED, Colombo (LK)

( * ) Notice: Subject to any disclaimer, the term of this patent is extended or adjusted under 35 U.S.C. 154(b) by 283 days.

(21) Appl. No.: 15/550,733

(22) PCT Filed: Feb. 15, 2016

(86) PCT No.: PCT/GB2016/050367
§ 371 (c)(1),
(2) Date: Aug. 11, 2017

(87) PCT Pub. No.: WO2016/128776
PCT Pub. Date: Aug. 18, 2016

(65) Prior Publication Data
US 2018/0242654 A1    Aug. 30, 2018

(30) Foreign Application Priority Data

Feb. 13, 2015  (GB) .................................. 1502426.8
Oct. 2, 2015   (GB) .................................. 1517413.9

(51) Int. Cl.
*A61B 5/00*     (2006.01)
*A41D 1/00*     (2018.01)
(Continued)

(52) U.S. Cl.
CPC ............ *A41D 1/005* (2013.01); *A61B 5/0022* (2013.01); *A61B 5/112* (2013.01); *A61B 5/1118* (2013.01);
(Continued)

(58) Field of Classification Search
CPC ..... A61B 5/0022; A61B 5/1118; A61B 5/486; A61B 5/7455; A61B 5/6844; A61B 5/112;
(Continued)

(56) References Cited

U.S. PATENT DOCUMENTS 10,154,694 B2 * 12/2018 Scheffler ................ A41D 1/002
2005/0097970 A1    5/2005 Nurse
(Continued)

FOREIGN PATENT DOCUMENTS

EP    2654030 A1    10/2013
GB    2515104 A     12/2014

*Primary Examiner* — Max F Hindenburg
(74) *Attorney, Agent, or Firm* — Snell & Wilmer L.L.P.

(57) ABSTRACT

A garment (100) for use in system for monitoring the technique of a user undertaking a physical activity which comprises a securing region for securing the garment against a part of the users body, wherein said securing region comprises an interface connector (18) suitable for connecting to a processing unit (200), and said garment further comprising at least one data transmission path (14) connected to said interface connector and suitable for connection to a sensor (12) and/or a control switch In use the garment enables the collection of data associated with the motion of the user, the comparison of this data with a biomechanical model of the exercise activity and the provision of a feedback response to the user. This enables the user to enhance their technique, and therefore their performance and reduce the likelihood of injuries.

18 Claims, 7 Drawing Sheets

(51) Int. Cl.
*A61B 5/11* (2006.01)
*A63B 24/00* (2006.01)

(52) U.S. Cl.
CPC ............ *A61B 5/486* (2013.01); *A61B 5/6804* (2013.01); *A61B 5/7455* (2013.01); *A63B 24/0062* (2013.01); *A61B 2503/10* (2013.01); *A61B 2562/04* (2013.01); *A61B 2562/046* (2013.01); *A61B 2562/227* (2013.01)

(58) Field of Classification Search
CPC .......... A41D 1/005; A41B 1/08; H01R 33/94; H01R 12/771
See application file for complete search history.

(56) References Cited

U.S. PATENT DOCUMENTS

| | | |
|---|---|---|
| 2007/0299325 A1 | 12/2007 | Farrell et al. |
| 2008/0287770 A1 | 11/2008 | Kurzweil et al. |
| 2008/0300503 A1 | 12/2008 | Lee et al. |
| 2009/0204013 A1 | 8/2009 | Muehlsteff et al. |
| 2009/0270708 A1 | 10/2009 | Shen et al. |
| 2010/0088803 A1 | 4/2010 | Orloff |
| 2010/0292050 A1 | 11/2010 | DiBenedetto et al. |
| 2011/0230985 A1 | 9/2011 | Niegowski et al. |
| 2012/0086550 A1 | 4/2012 | LeBlanc et al. |
| 2014/0172134 A1 | 6/2014 | Meschter |
| 2014/0199672 A1 | 7/2014 | Davidson |
| 2014/0206948 A1* | 7/2014 | Romem ............... A61B 5/0022 600/301 |
| 2015/0040282 A1 | 2/2015 | Longinotti-Buitoni et al. |
| 2015/0047091 A1* | 2/2015 | Fournier ............... H02G 15/013 2/69 |
| 2015/0074866 A1* | 3/2015 | Diakite ............... A41D 27/208 2/69 |
| 2016/0000379 A1* | 1/2016 | Pougatchev ......... A61B 5/7275 600/479 |
| 2016/0113581 A1* | 4/2016 | Amir ................... A61B 5/6804 600/301 |

* cited by examiner

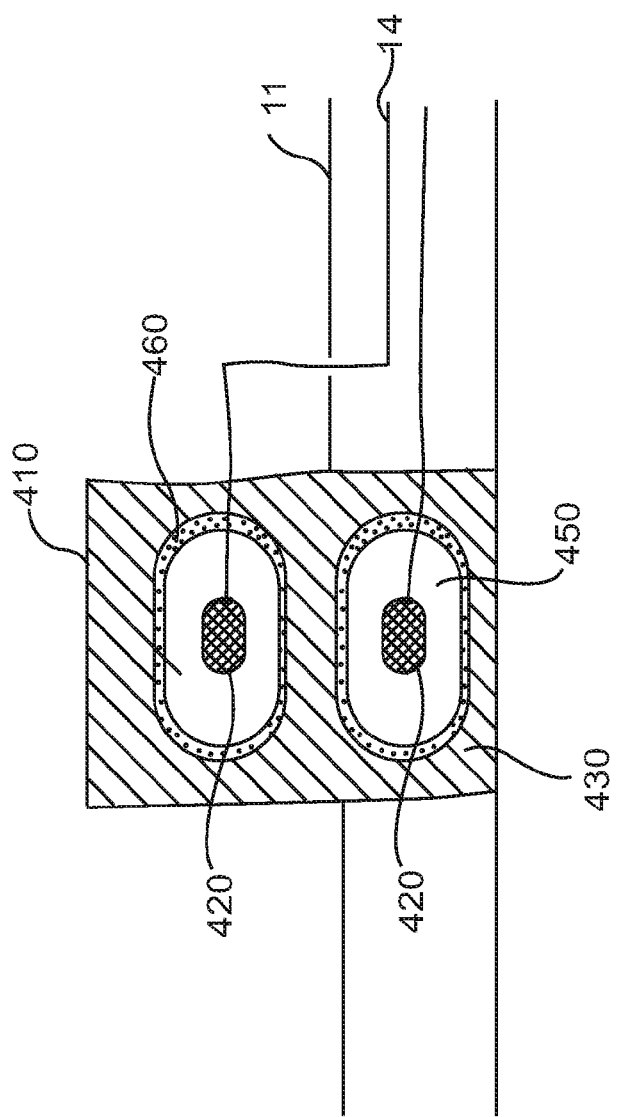

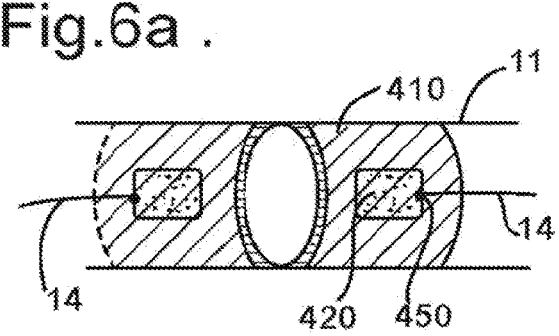
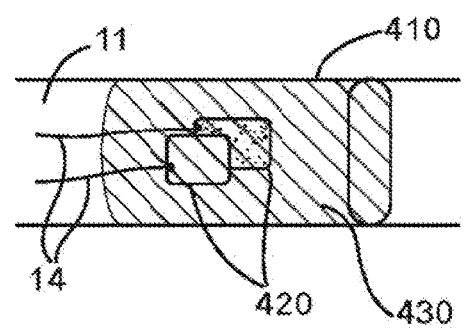
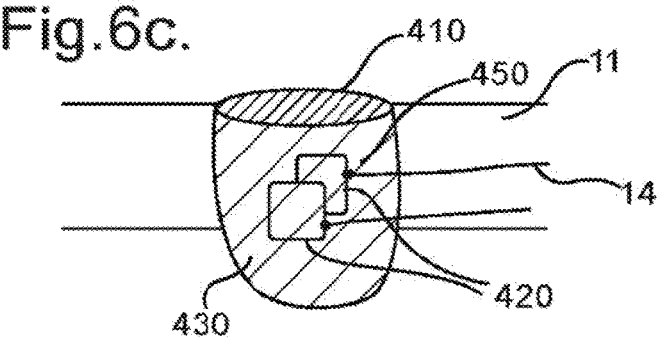

SMART APPAREL

This invention relates to systems and methods for monitoring the technique of a user undertaking a physical activity and to garments suitable for use in such systems and methods. More particularly, the invention relates to systems and methods which provide feedback to the user during the physical activity and to garments suitable for use in such systems and methods.

There is a significant proportion of the population who regularly undertake an exercise activity. For example, there are 9 million core recreational runners in the US, who typically participate in multiple races each year. Often runners rely on an instinctive feel for their own physiological measures affecting running, as well as for nutrition and conditioning through years of running experience. But they have minimal opportunity to identify whether they are running with correct technique which can be crucial to achieving an enhanced performance as well as to prevent and/or to reduce the likelihood of injuries.

Usually runners or participants in other exercise activities do not have access to a personal coach to observe and advise, and even if they do, typically the coach is not present at all stages of the activity. For example, runners do not often run with their coach, and therefore are unable to obtain advice as to their running technique at the crucial stages of a run when they are fatigued and likely to lose form. The runner may consider attending a runner injury clinic, but these may not be conveniently located and may also be some distance away.

It is known to incorporate sensors into exercise equipment and clothing, for example to detect motion of the user. The data collected during a physical activity is typically uploaded by the user after completion of the physical activity for analysis, for example to determine the distance run or the number of steps taken, or may be analysed by remote monitoring by a third party.

There is a need for the provision of enhanced systems and methods which enable real-time feedback on form and technique during a physical activity and which can therefore help to improve performance and to prevent and/or to reduce injury.

In an aspect of the invention, there is provided a system for monitoring the technique of a user undertaking a physical activity, the system comprising at least one garment worn by the user, the garment incorporating or carrying at least one sensor for the detection of at least one parameter relating to the motion of the user; a processing unit configured to receive information about the at least one parameter from the at least one sensor, to compare the or each parameter with at least one aspect of a biomechanical model of the physical activity, and to determine if a feedback response is required; and means embedded in or carried by the garment for providing the feedback response to the user during the physical activity. In some cases, the biomechanical model may be generated by analysis of coaching recommendations, or analysis of physical activity, or models of physical activity.

The system enables the user to receive real-time feedback during a physical activity, such as running or running based sports, walking, swimming, throwing sports, yoga, pilates, cycling, weight-lifting, etc. In one embodiment of the invention, the physical activity is not running or a running based sport. The system also enables real-time feedback to be provided to a user undertaking a physical activity at work, such as lifting, pulling or carrying. The feedback provided enables the user to enhance their technique, for example in the case of a runner, relating to their running form, such as knee positioning, hip positioning, stride length, dynamics and duty factor, parameters related to the movement of the pelvis during running in three dimensions, foot strike parameters etc., or a combination of these factors. Maintaining and/or improving technique during a physical activity can help to enhance performance, for example enhance endurance and/or speed and reduce the likelihood of injuries.

The system incorporates at least one garment which is worn by the user, which could be, for example, a pair of shorts, a vest, a t-shirt, training top, leggings, a weightlifting belt, or any other garment suitable for use during a physical activity. In some embodiments the garment may be a base layer, or other body fitting apparel. Preferably the garment is close fitting to the body of the user, for example close fitting to the torso. Alternatively, the garment may be a looser fitting garment with a part of the garment that is secured to the body (preferably on the torso), such as a loose fitting pair of shorts with a fitted waistband for example. The system may incorporate a combination of garments, for example a combination of a garment worn on the lower half of the user's body and a garment worn on the upper half, such as a pair of shorts or leggings and a t-shirt or training top. This enables sensors to be placed in positions to monitor motion in both the upper body, such as the arms, and lower body, such as the legs.

The garment incorporates or carries at least one sensor which detects at least one parameter relating to the motion of the user. Such parameters may relate, for example, to the speed, direction of movement, and/or acceleration of at least one part of the body of the user or to the relative speed, direction of movement and/or acceleration of two or more parts of the body, or other kinematic data. The sensor may, for example, be an accelerometer or a gyroscope. The system may use a combination of sensor types, for example a combination of at least one accelerometer and at least one gyroscope. The use of at least one sensor incorporated or carried within a garment provides more accurate data at a specific body location rather than an approximation.

The garment also includes a processing unit which is configured to receive information about the at least one parameter from the at least one sensor. The sensors maybe connected to the processing unit via at least one data conduction path, or as an alternative the sensors may be wirelessly connected to the processing unit. Preferably the sensors are connected to the processing unit via at least one data transmission path embedded within the garment. The data received from the one or more sensors is compared to at least one aspect of a biomechanical model of the physical activity to determine if a feedback response is required.

Preferably the biomechanical model comprises a database of kinematic parameters and optimal ranges for each of the parameters. The biomechanical model may be generated by an analysis of the motion of a plurality of individuals undertaking the physical activity, such as an analysis of the motion of a cohort of high performance individuals and a cohort of low performance individuals. Individuals to be included in each cohort may be selected, for example, using sporting performance criteria or an analysis of past injury record.

This model may for example be a biomechanical model of running. Such models are known, for example as disclosed in Cavanagh, P., Kram, R., 1989. Stride length in distance running: velocity, body dimensions and added mass effects, in: Cavanagh P R, Editor. Biomechanics of Distance Running. Human Kinetics, pp. 35-63; Cavanagh, P. R., Kram, R., Rodgers, M. M., Sanderson, D. J., Hennig, E. M., 1985.

An Approach to Biomechanical Profiling of Elite Distance Runners. International J. Sports Biomech. 13, 397-406; Cavanagh, P. R., Pollock, M. L., Landa, J., 1977. A biomechanical comparison of elite and good distance runners. Ann. N. Y. Acad. Sci. 301, 328-345; Boyer, K. A., Freedman Silvernail, J., Hamill, J., 2014. The role of running mileage on coordination patterns in running. J. Appl. Biomech. 30, 649-654.

The processing unit may, for example, compare the data received with an optimal range relating to an aspect of the biomechanical model and therefore determine whether a feedback response is required, for example in relation to the stride length of a runner, a determination as to whether the stride length is outside an optimal range.

The optimal range may be adjusted, for example, based on personal data entered by the user, for example relating to height or weight. This range may also be adjusted based on contextual data, such as data collected over the period of the physical activity.

In the case where the data received being outside of an optimal range, the processing unit is configured to decide whether a feedback response is required. The processing unit may be configured to determine whether the provision of feedback relating to a single aspect of the biomechanical model would negatively impact on overall technique of the user, and therefore to determine whether to provide the feedback response. The processing unit may also be configured to determine if the system is currently providing a feedback response relating to an alternative aspect of the biomechanical model, and then decide whether to place the new feedback response in a queue or not to deliver the feedback response.

The system also comprises a means for providing a feedback response to the user during the physical activity. This feedback may, for example, be provided by a means for providing a mechanical stimulus, for example by at least one actuator. Preferably the actuator is one or more of haptic actuator, thermal actuator, peltier tiles, TENS actuator, electro-active polymer or micro-piezo actuator. This type of feedback response is not intrusive and enables the user to concentrate on the physical activity, without requiring reference to an audio or visual feedback mechanism.

The means for providing a mechanical stimulus, such as at least one haptic actuator, may be embedded in one or more garments forming part of the system. The means for providing a mechanical stimulus maybe connected to the processing unit via at least one data conduction path, or as an alternative may be wirelessly connected to the processing unit. Preferably the means for providing a mechanical stimulus is connected to the processing unit via at least one data transmission path embedded within the garment. This enables the user to undertake the physical activity without the requirement to carry additional system components. The means for providing a mechanical stimulus, such as a haptic actuator, may be positioned to provide a feedback response at the location of the body at which a correction of technique is required, thereby enhancing the effectiveness of the feedback and helps the wearer to distinguish the action needed by them.

The feedback may also be by audio or visual means, for example through headphones worn by the user and/or a visual display. This feedback mechanism may be provided through a connection between the processing unit and a mobile electronic device, such as a smartphone, for example by means of a Bluetooth or other wireless connection. The system may be configurable to allow the user to customise the feedback response, for example, enabling the selection of the means of feedback response, or the priority of the delivery of feedback relating to different aspects of the biomechanical model.

The system may incorporate both mechanical and audio feedback mechanisms, for example through the combination of one or more haptic actuators and an audio and/or visual feedback mechanism.

The system may also be configured to enable the user to review analytical data relating to the physical activity. For example, during or after a physical activity data may be transferred to a software application, which may be configured to enable, for example, visualisation of post-activity analytics, a comparison with historical data etc.

In another aspect of the invention there is provided a garment for use in a system for monitoring the technique of a user undertaking a physical activity, the garment comprising a securing region for securing the garment to a part of the users body, wherein said securing region comprises an interface connector suitable for connecting to a processing unit, and said garment further comprising at least one data transmission path connected to said interface connector and suitable for connection to a sensor and/or a control switch. Preferably, the at least one data transmission path is embedded within the garment, for example encapsulated on the inside of the garment.

The garment may be, for example, a garment worn on the lower half of the user's body, for example a pair of shorts, tights or leggings or a garment worn on the upper half of the user's body, such as a t-shirt or other running or training top or any other garment suitable for use during a physical activity. In one embodiment of the invention, the garment is not a running garment. In some embodiments of the invention, the garment is typically a base layer. Preferably the garment is close fitting to the body of the user. Alternatively, the garment may be a looser fitting garment with a part of the garment that is secured to the body, such as a loose fitting pair of shorts with a fitted waistband for example. Preferably, the garment incorporates at least one sensor, which may be incorporated in the securing region, where the sensor detects at least one parameter relating to the motion of the user. Such parameters may relate, for example to the speed, direction of movement, and/or acceleration of at least one part of the body of the user or to the relative speed, direction or movement and/or acceleration of two or more parts of the body. The sensor may, for example, be an accelerometer or gyroscope. The garment may include a combination of sensor types. The sensor may be connected to the interface connector by at least one data path.

Preferably, the sensors may be fabricated such that they can be embedded and/or encapsulated partially or entirely within the garment. In some cases they may be formed as flexible electronic boards, or as a system in foil sensor for example.

The garment may additionally comprise means for providing a feedback response to the user during the physical activity. This feedback may, for example, be provided by a means for providing a mechanical stimulus, for example by at least one actuator, where the actuator maybe one or more of haptic actuator, thermal actuator, peltier tiles, TENS actuator, electro-active polymer or micro-piezo actuator. The actuators may be formed from electro-active polymer, or may be printed directly onto the textile material that will form the garment, they may then subsequent be encapsulated to hold the actuator within the garment. Preferably, the actuator is embedded in the garment, and maybe connected to the interface connector in the securing region.

The garment may also be provided with indicators such as LED or OLED devices to provide the facility for in-built lighting.

The garment may have a flexible dock area that can receive a removable processor module that can connect to the sensors and/or actuators in the garment. The flexible dock may be in the securing region, or in another region of the garment, for example, located within a pocket of the garment. A pouch may be incorporated within the garment to hold the processing unit. The pouch is located so that a secure connection may be maintained with the flexible dock, and may be adjacent to or incorporate the flexible dock. The flexible dock may be provided with grip material to secure the removable processor in place. Preferably, this may use a silicone gripper, covering some, or all, of the interior of the flexible dock.

Preferably, the flexible dock may be constructed of regular stretchable material with properties the same or similar to the remainder of the garment. In some embodiments, the flexible dock may be provided with flexible connection patches, for connecting an inserted processor model to sensors and/or actuators in other parts of the garment. The flexible connection patches may be formed from one or more of: flexible metal foils, conductive fabric patches, a conductive embroidery patch, conductive ink print, silver (Ag) print, conductive silicone, conductive glue or polymer patches.

The flexible dock may have a slit opening, pillowcase opening, Velcro snap opening or top (horizontal) opening for receiving the processor module.

The garment also includes an interface connector suitable for connecting to a processing unit. This connector enables the electrical and data connection between the processing unit and the at least one sensor or a control switch. The connector may be arranged to enable a releasable connection between the garment and the processing unit, for example using snap connectors, such as magnetic snap connectors. This enables the processing unit to be exchanged between garments and removed before garment washing.

The interface connector provides a connection to the at least one sensor via at least one data transmission path which may be embedded within the garment. This data transmission path enables transmission of data between the or each sensor and the processing unit. The data transmission paths may also provide an electrical connection between the system components. The data transmission paths may also connect the processing unit to the means for providing a feedback response to the user, such as an actuator. As an alternative, the or each sensor may be wirelessly connected to the interface connector.

The garment may also be provided with a control switch connected to said interface connector. The control switch may control sensors/actuators in the garment or in a processing unit. The control switch may also be used to control and adjust the feedback response.

In a further embodiment of the invention there is also provided a securing region for attachment to a garment that may be used in physical activity, wherein said securing region secures the garment against a part of the users body and comprises an interface connector suitable for connecting to a processing unit, and said securing region further comprising at least one data transmission path connected to said interface connector and suitable for connection to a sensor and/or a control switch. Preferably, the securing region will be the waistband of the garment. The securing region may have a flexible dock area that can receive a removable processor module that can connect to the sensors and/or actuators in the garment. The flexible dock may be provided with grip material to secure the removable processor in place. Preferably, this may use a silicone gripper, covering some, or all, of the interior of the flexible dock.

Preferably, the flexible dock may be constructed of regular stretchable material with properties the same or similar to the remainder of the garment. In some embodiments, the flexible dock may be provided with flexible connection patches, for connecting an inserted processor model to sensors and/or actuators in other parts of the garment. The flexible connection patches may be formed from one or more of: flexible metal foils, conductive fabric patches, a conductive embroidery patch, conductive ink print, silver (Ag) print, conductive silicone, conductive glue or polymer patches.

The flexible dock may have a slit opening, pillowcase opening, Velcro snap opening or top (horizontal) opening for receiving the processor module.

In a further aspect of the invention there is provided a method for monitoring the technique of a user undertaking a physical activity, the method comprising the steps of:
(i) determining at least one parameter relating to the motion of the user with a sensor incorporated within or carried by a garment worn by the user, such as a garment as defined herein;
(ii) comparing the or each parameter with at least one aspect of a biomechanical model of the physical activity to determine whether a feedback response is required;
(iii) providing the feedback response to the user during the physical activity, wherein said means for providing feedback is embedded in or carried by said garment.

Preferably, the feedback response is provided by at least one actuator embedded in or carried by the garment. The at least one actuator may be one or more of a haptic actuator, thermal actuator, peltier tiles, TENS actuator, electro-active polymer or micro-piezo actuator.

Preferably the biomechanical model is generated by an analysis of the motion of a plurality of individuals undertaking the physical activity, such as an analysis of the motion of a cohort of high performance individuals and a cohort of low performance individuals. Individuals to be included in each cohort may be selected, for example, using sporting performance criteria or an analysis of past injury record. In one embodiment of the invention the physical activity is not running or a running-based sport.

In one embodiment of the systems and methods described herein, the physical activity is cycling. The garment may for example be a pair of cycling shorts, such as bib shorts, with at least one embedded or detachable sensor. The sensor may be positioned, for example, in the back of the waistband and/or the hem of the legs of the shorts. Preferably, at least one sensor is positioned in the back of the waistband and the hem of each leg. This enables parameters relating to the overall posture of the cyclist and the cycling motion of the legs to be captured. The parameters may be compared to a biomechanical and aerodynamic model of cycling and feedback provide to the user, for example relating to the ideal posture to achieve the best yield and aerodynamic performance, and/or optimal power output at the legs. This feedback may be delivered via haptic actuators on the hems of the legs of the shorts. The system may be connected to a portable electronic device, such as a smart phone, which may be carried in the cycling garments or on the bicycle. Real-time feedback may be provided via the portable electronic device in the form of audio and/or visual feedback.

In another embodiment of the systems and methods described herein, the physical activity is weight lifting. This embodiment comprises at least one garment worn on the torso of the user in which at least one sensor is incorporated, for example a base-layer garment or a weightlifting belt, or the system may comprise a combination of a base-layer garment and a weightlifting belt. The system may also comprise other accessories incorporating at least one sensor, such as knee-pads or gloves. The system comprises means for providing feedback to the user embedded in or carried by at least one garment, for example at least one actuator embedded in the base-layer and/or the belt. The means for providing a feedback response provides an alert to the user when a potentially harmful lifting form is detected. In the regular use, the system may record, for example the efficiency, adherence to form and the repetitions of a weight-lifter, and may be configured to provide graphical feedback to the user post-lifting to help the user adjust and improve lifting form.

In a further embodiment of the systems and methods described herein, the physical activity is a physical activity carried out at work, such as by workers in warehousing and logistics, for example lifting, pulling or carrying. This embodiment comprises at least one garment worn on the torso of the user in which at least one sensor is incorporated, for example one or more of a base-layer garment, overalls, a belt etc. the system may also comprise other accessories incorporating at least one sensor, such as knee pads or gloves. The system comprises means for providing feedback to the user embedded in or carried by at least one garment, for example at least one actuator embedded in the base-layer and/or the belt. The means for providing a feedback response provides an alert to the user, such as a vibratory alert, if an incorrect posture during a particular motion is detected. The systems and methods can therefore help to reduce injury. In addition data captured by the system may be accumulated and analysed to track patterns and trends in work ergonomics, for example to provide training wherever needed and also to manage insurance costs.

The present invention will now be described, by way of example only, with reference to the accompanying drawings, in which:

FIG. 5 shows a schematic representation of the flexible dock provided in the garment;

Figure 7A:
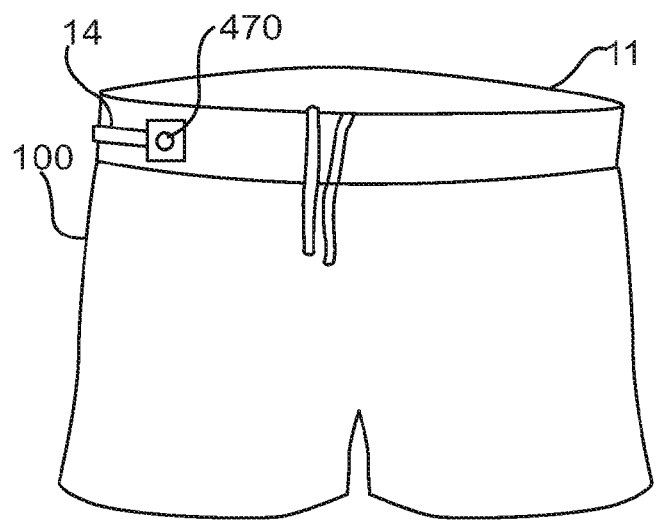
Figure 8:
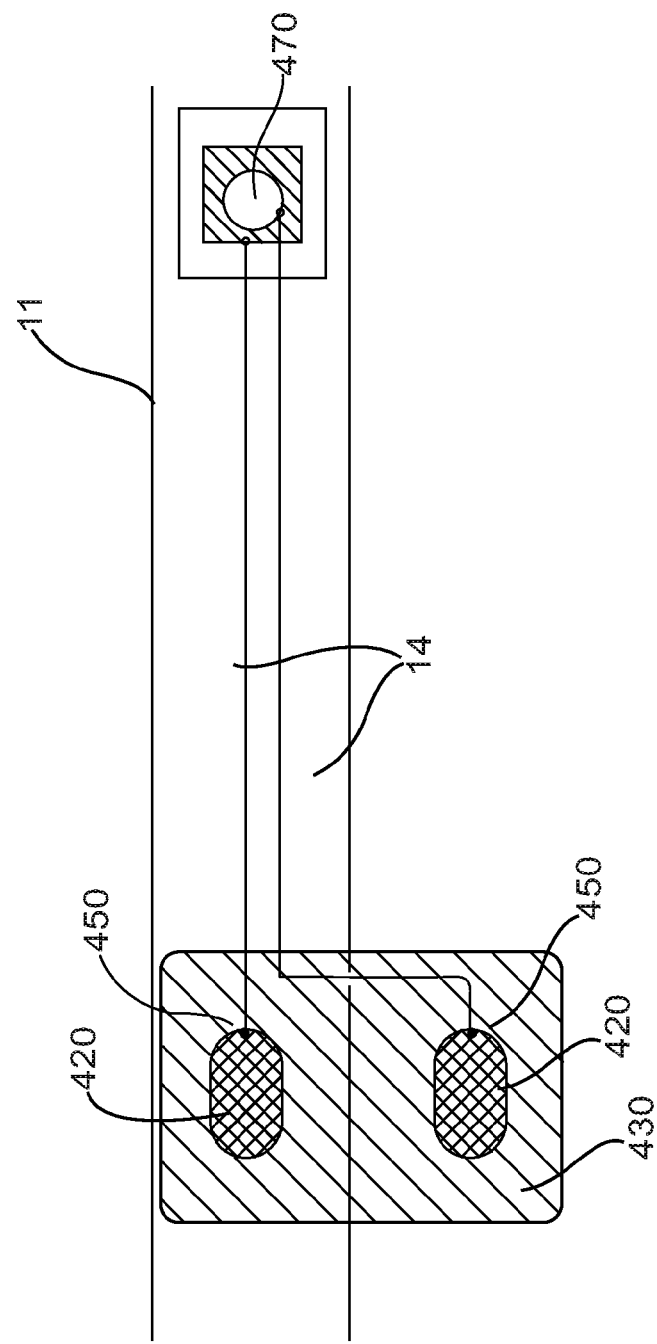
Figure 9:
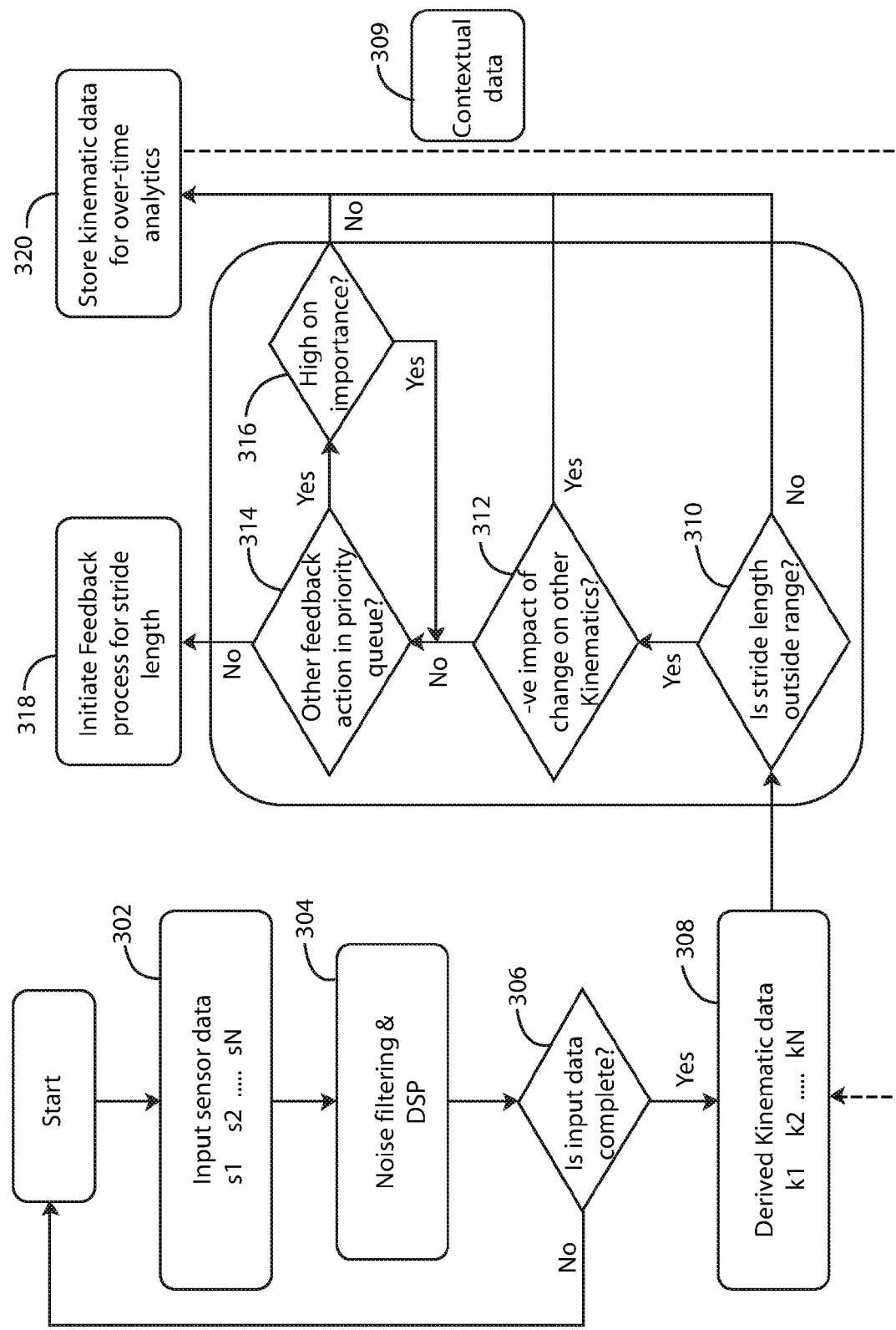

FIGS. 6(a)-(c) show different types of flexible dock that may be provided in the garment;

FIGS. 7(a) and (b) and front and rear views of a garment with a waistband;

FIG. 8 is a detailed view of the waistband of the garment;

FIG. 9 shows an embodiment of a logic flow for determining whether a feedback response is required.

Figure 1:
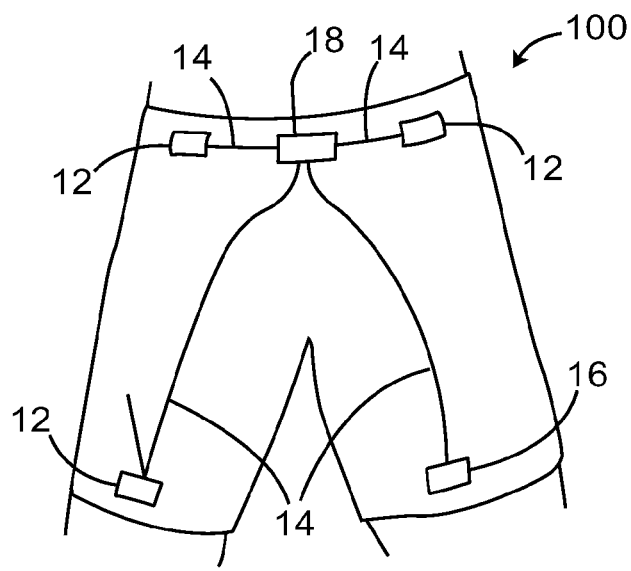
FIG. 1 shows a schematic representation of a garment according to a first embodiment of the invention.

FIG. 1 shows a garment 100 suitable for running which includes sensors 12. The sensors 12 detect one or more parameters relating to the motion of the user which are important to running form and technique. The sensors 12 are connected to an interface connector 18 by data transmission paths 14 which are also used to provide power to the sensors 12. The data transmission paths 14 are encapsulated on the inside of the garment 100. The garment 100 also includes a feedback actuator 16 which provides a feedback response to the user regarding form and technique whilst the user is running. In this embodiment the actuator is a haptic actuator 16 connected to the interface connector 18 by a data transmission path 14. In one instance the feedback actuators can be micro haptic motors, in another they can be thermal actuators or peltier tiles or Transcutaneous Electrical Nerve Stimulation (TENS) actuators, electro-active polymers or micro piezo-actuators.

Figure 2:
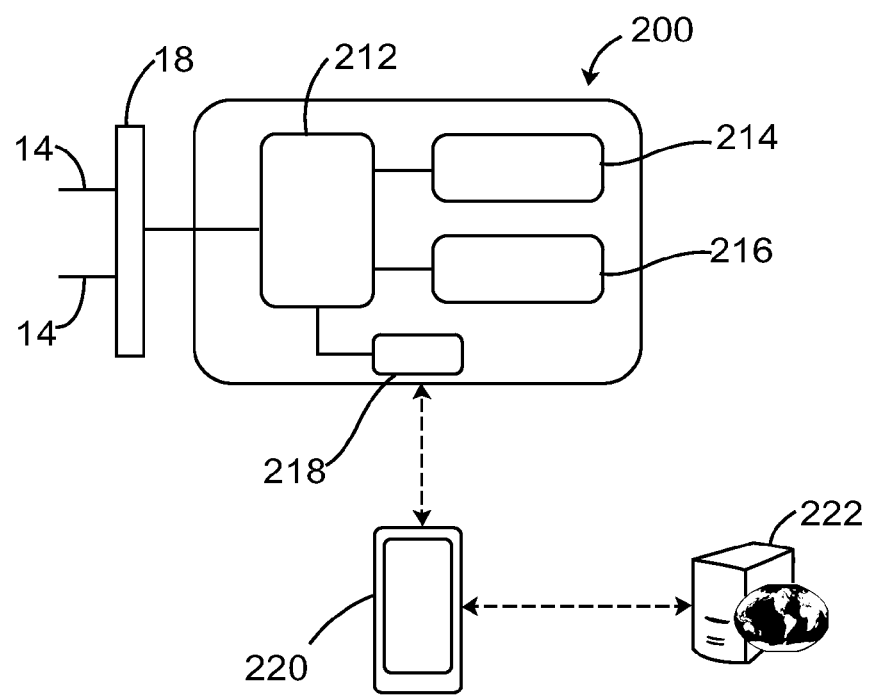
FIG. 2 shows a schematic representation of a processing unit for use in a system according to the invention.

The interface connector 18 enables the releasable connection of processing unit 200 (FIG. 2) to the garment 100. The interface connector 18 enables data and power transfer between the processor module 200 and the sensors 12 (not shown in FIG. 2) and the haptic actuator 16 (not shown in FIG. 2) via the data transmission paths 14. In use, the processor module 200 activates the sensors 12 and the feedback actuator in the garment. The processor module 200 comprises a processor 212, a memory module 214, a battery 216 and a wireless enabling unit 218. The processor 212 receives data from the sensors 12 and compares the parameters with at least one aspect of a biomechanical model of running in order to monitor current running form and technique. The processor 212 determines whether a feedback response is required.

The memory module 214 is used, for example, to store relevant data points which can be used in a post-run analysis of form and technique and/or to provide contextual data to adjust the analysis carried out by the processor module 200 during the run. The memory module 214 can store data from multiple activity instances until, for example, they are transmitted to an external device.

The processor module 200 may be connected to a mobile phone or other portable electronic device 220 via wireless enabling unit 218, which may for example set up a Bluetooth connection. The portable electronic device 220 is provided with a software application which can process data accumulated during the physical activity and provide post-run and historical analysis, tips and information on the users form and technique. The software application may use cloud based storage 222 as a back-up repository for this accumulated data as well as a platform to share this data with other applications, devices or human coaches as selected/configurable by the user. The wireless connection between the portable electronic device 220 and the processor module 200 may also be used to update software on the processor module 200 (including but not limited to the biomechanical model embedded in the processor module 200).

This feedback response may be delivered via the haptic actuator 16 in the garment or, if the processor module 200 is connected to a portable electronic device 220 whilst the user is running, then the software application may deliver audio and/or visual feedback, or feedback though, for example, vibration of the portable electronic device 220.

In use, the user will download a software application 230 to the portable electronic device 220 and will connect the processor module 200 to the software application (for example via Bluetooth) and enter their personal variables to customize the feedback response to their profile.

The user will attach the processor module 200 to the garment 100 prior to starting the run and can optionally connect the processor module 200 to the software application 230 if the user plans to take a portable electronic device 220 on the run.

The user will run as usual. The system will monitor the form and technique of the user and provide improvement feedback via the haptic actuator 16 (the user can customize the frequency and type of the feedback via the software application 230 or turn off feedback from the processor module 200 as their preference). Optionally, the user can receive feedback in audio/visual form from the software application if it's connected to the processor module 200 while running. This feedback may, for example, be delivered through headphones.

The user may elect to adjust their running form or technique according to the feedback given. The system will learn some of the intrinsic and unique features of the user in order to adapt future feedback. The user will finish the run.

The user can connect the processor module 200 to the software application (if not done before) to transfer the run data to the application. The user will review post-run analytics and historical data on the software application. If the processor module 200 is not connected to the software application after a particular run, it will retain the data until the connection is made.

In terms of weight, wearability and comfort garment 100 with sensors 12, feedback actuator 16 and data transmissions paths 14 is designed and produced to be virtually identical to a regular unmodified garment, without any of these additional elements, making the sensors 12, actuators 16 and conductive paths 14 almost invisible to the wearer. Preferably garment 100 is fully washable and maintainable as regular apparel.

Garment 100 is provided with a flexible dock 410 which allows a processor module 200 to be easily connected to garment 100. Processor module 200 may house the processing, powering, memory and wireless transmission elements of the overall system which activates sensors 12 and actuators 14 in the garment 100 once connected. A biomechanical model is typically provided on the processor to interpret signals from sensors 12, to identify the current running form and technique of the wearer and give real-time 'course correction' feedback as well as retain the relevant data points to be used in a post-run detailed analysis of form and technique. The user is able to control the feedback and the status of the system via the interaction with the detachable module or a separate control mechanism built on to the garment.

Figure 3:
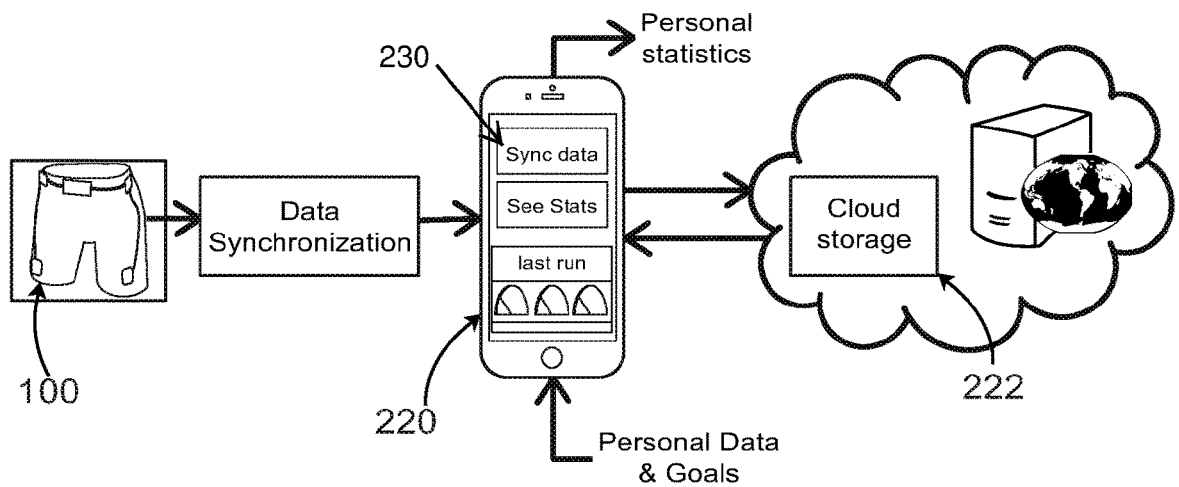
FIG. 3 shows the overall system of an embodiment the invention.

As shown in FIG. 3, the processor module 200 can store data from multiple activity instances until they are transmitted out of the module to a mobile phone application 230, for example, which is typically connected via wireless (Bluetooth) to the module. If the module is connected in real-time to a mobile phone 220 while the wearer is running, then the mobile application 230 is capable of delivering further real-time feedback (typically audio and/or visual) apart from the simpler haptic feedback that is built into garment 100 (or the module).

In addition, the mobile phone application 230 is capable of delivering more in depth post-run and historical analysis, tips and information on the user's form and technique. The application will use the cloud 222 as a backup repository for this data as well as a platform to share this data with other applications, devices or human coaches as selected/configurable by the user. The user will use the mobile app 230 as their interface to the smart garment system and customize/personalize several variables through the app as well.

Figure 4:
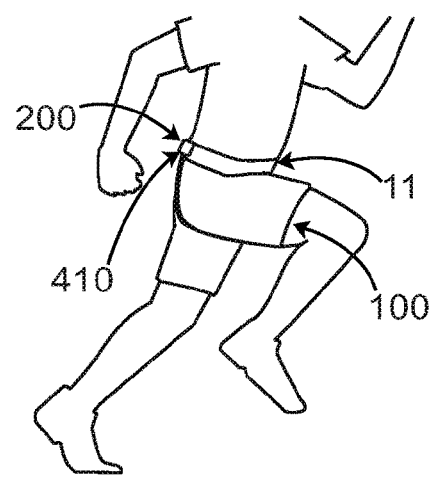
FIG. 4 shows a representation of an embodiment of a garment with a waistband, according to the invention.

FIG. 4 shows one possible embodiment of the system where the motion sensors 12 are located in a detachable processor module 200 which interfaces with the garment 100 via a flexible dock 410 in the waistband 11 of garment 100. Even though the motion sensors 12 are located in a single place (as opposed to a network of sensors distributed over different regions of garment 100) the sensors 12 are able to distinctly capture multiple kinematic variables related to the running motion from that single location. Preferably, the location is an optimized location in the whole body for such motion capture, being based on the Posterior Sacroiliac (PSI) ligament area of the lower back which is easily accessible through the garment waistband. Furthermore, a user is able to interact with the detachable processor module 200 in the waistband 11 via control mechanisms built in to the garment 100 at accessible locations in the garment, preferably, but not exclusively the front and side of the garment. The user controls (not shown) may include, but are not limited to, turning the sensors and feedback system on and off, muting or adjusting the volume of the feedback, getting on-demand feedback etc. In a preferred embodiment, the control mechanism is a switch connected to the flexible dock 410 and the processing module 200 via data and conductive paths 14 which transmit the control signals back and forth. The full system including the electronic circuitry in garment 100, the control switch, the flexible dock 410 and the embedded module 200 can be washed and maintained like a regular garment. In this embodiment, basic feedback from the system is given via actuators 16 in garment 100, alternatively, the feedback actuators maybe found in processor module 200. A biomechanical model and appropriate algorithm reside in a separate mobile device app 230 which is wirelessly connected to the module 410. By use of the biomechanical model and algorithms the mobile app 230 provides detailed kinematic feedback and post-run advice to the user.

Typically, sensors 12 can be fabricated in flexible electronic boards (PEN boards) or as System In Foil (SIF) which is then embedded between two layers of polymer film. These electronic sensor components in turn can be integrated to the underside/inside of the apparel in the optimum locations for sensing and encapsulated in a variety of ways, such that the wearer does not feel any difference with conventional apparel. Once the sensors 12 are fully encapsulated garment 100 may also be washed and maintained as regular apparel.

Thereafter, sensors 12 can be connected by conductive/data paths 14 to activate them and to obtain data signals. The conductive/data paths 14 will connect each sensor 12 to the textile-electronic interface (or the dock 410) where the detachable electronic module 400 will power and drive the sensor network. The interconnections between the sensor 12 and conductive paths 14 (and also between the interface dock and conductive paths) can also be achieved in various different ways.

The layout of the sensors 12 within the garment 100 is typically governed by a biomechanical model. This will determine where sensors 12 should be placed in the garment (according to what the sensor is sensing). Typically, the number of sensors 12 is between one to four. Sensors in excess of four will generally be redundant because of the ability to detect multiple kinematic variables from a single location.

In manufacturing, the sensors 12 and textile circuitry (conductive/data paths 14 & interconnections) can be applied both in panel form, before garment construction as well as in garment form, after the construction of garment 100. In the latter process, the application method can be automated to apply and integrate the pre-determined sensor network 12 on the garment 100 in a single step.

Different sensor types that may be incorporated for the running application include one or more of; motion processing sensors (IMU's); accelerometers, gyroscopes, magnetometers or any combination thereof; piezo-electric sensors that could detect relative moment of limbs and joints; piezo-chromic sensors that could indicate a colour change based on movement; capacitive sensors that can detect relative movement; PPG sensors that can detect Heart Rate, respiration and pulse; EMG sensors that can detect muscle movement & activity.

Feedback actuators 16 may be fabricated in flexible PCB or as SIF components and can be integrated to critical and sensitive locations on the inside surface of garment 100 to provide real-time feedback to the wearer.

Preferably, the feedback actuators 16 are Electro-Active Polymer paste and can be printed directly in to textile material akin to a conventional print. In any case, the wearer will not be able to distinguish between actuator embedded/printed garments as against conventional apparel. As before, once the actuators are encapsulated the apparel could also be washed and maintained as regular apparel.

Once the feedback actuator 16 is integrated to the garment 100 surface in the appropriate location, they are linked to the control interface via conductive paths 14 that transmit the control signals for feedback actuation.

In the manufacturing process, any of sensors 12, feedback actuators 16, and textile circuitry (conductive/data paths 14 & interconnections) can be integrated into the garment 100 in either panel form before garment construction, or complete garment form, in the latter case as a single step process. In some cases, the application method can be automated to apply and integrate the pre-determined sensor network 12 on the garment 100 in a single step.

Traditionally the interface or the connection between a detachable electronic module and the textile/apparel has been via a rigid, or at least semi-rigid connectors that were used to provide good contact and stability to the external module.

In this embodiment of invention, electronic integration is via a flexible dock 410 where the processor module 200 with multiple exposed contacts is inserted and the connections are made via corresponding flexible connection patches 420 built in to the textile, as shown in FIG. 5. In some alternative embodiments it may be a power module, memory module, activation module etc. that is inserted into the flexible dock 410, as well as or instead of the processor module 200. The desired quality of electronic contact and the stability thereof is provided by a) defining the properties (thickness, modulus etc) of the material of the flexible dock/pocket and b) the shape and engineered construction of the same which creates a snug fit with optimal tension to hold the electronic module in place. The complete construction of the dock/pocket is based on regular stretchable, flexible textile type material that retains the properties of the rest of the apparel, so that the wearer will be oblivious to any un-apparel like elements in the garment.

In one embodiment, the flexible dock 410 is a pocket created on the waistband 11 of the running apparel where waistband 11 provides optimum support and stability to this type of flexible dock implementation. This is due to its nature of a) being placed at a more stable part of the body, b) having multiple layers of material within it and c) having thicker, elastic-like material within it. In this embodiment, the flexible dock 410 is created on the elastic (along with the other elements of the textile circuitry) and finished with the construction of the waistband using the outer (covering) material.

In a preferred embodiment of the invention the flexible dock 410 consists of a carrier material to construct the dock, in the shape and orientation of the final construction. In many embodiments this is the same as the body material of the garment. The flexible dock is typically provided with at least two (or multiple) conductive connection patches 420 from options described below. These will connect with corresponding contacts of the electronic processor module 200. Interconnections 450 join each connection patch 420 with a conductive/data path 14. There are multiple options for the flexible conductive connection patches used within the flexible dock 410. Some examples are; Flexible metal foil (print/heat transfer); Conductive fabric patch; Conductive yarn embroidery patch; Conductive ink/Ag (silver) print; Conductive silicone/polymer patch.

Interconnections 450 may be formed from options including conductive yarn bar tack, embroidery, conductive glue sealing etc. The carrier material may additionally be provided with contoured bonding tape or contoured stitch construction for the dock 410 to adhere to the shape of processor module 200. This provides fit and stability for the processor module 200 and connections in use. Optionally, silicone gripper 460 is printed in the appropriate shape to create additional friction within the flexible dock 410 to prevent slippage or movement of the module 200 in the dock 410. In the final construction, the flexible dock 410 will be closed along the contoured seams leaving an opening for the electronic processing module 200 to be inserted.

Within the same embodiment, the flexible dock 410 can take multiple outer appearances depending on the type and size of processor module 200, the ease of insertion/removal required, level of stability required and the orientation of the opening required. Some different options for the opening for the flexible dock 410 are shown in FIG. 6 and include; slit opening (middle or side) (FIG. 6(*a*)); pillowcase opening (FIG. 6(*b*); velcro snap opening; top (horizontal) opening (FIG. 6(*c*). In FIG. 6(*a*), the processor module 200 will be inerted in the middle of the flexible dock 410, in nfgure 6(*b*), the processor module is inserted through the rounded rectangular opening on the right hand side of flexible dock 410, and in FIG. 6*c* the processor module 200 will be inserted into the opening in the top of flexible dock 410. In all cases, the processor module 200 will have exposed contacts that will contact connection patches 420 within the flexible dock 310.

Figure 7B:
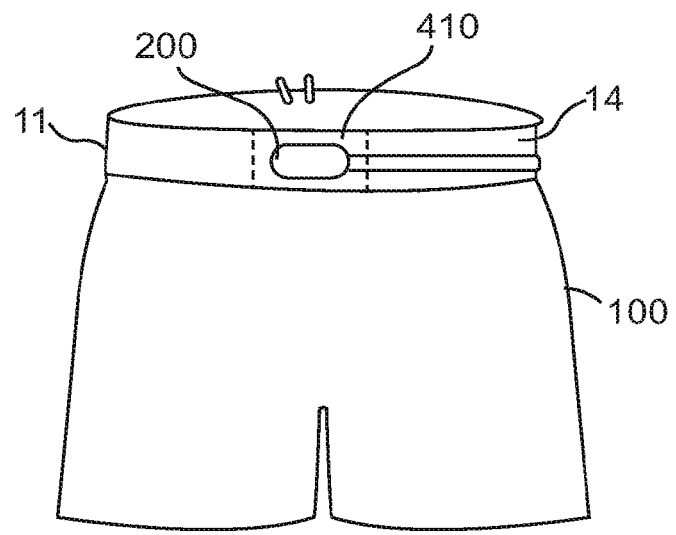

As described, the electro-mechanical system of this invention can be used in any garment 100 with a waistband 11. FIGS. 7(*a*) and (*b*) show front and rear views of a pair of shorts with a waistband 11. The shorts are provided with a switch 470 on the front of the waist band connected by a data path 14 to the electrical connection patches 420 in flexible dock 410. This is also shown in more detail in FIG. 8. Preferably the data path 14 is embedded within the waistband 11. Processor module 200 will be inserted into flexible dock 410 and is electrically connected to switch 470, via the connection patches 420, and the corresponding contacts on processor module 200. The wearer will be able to control the processor module 200 and adjust the feedback as required via the switch 470 on the garment 100. In this embodiment of the invention, all the sensors 12 and the feedback actuators are located within the processor module 200. The flexible dock 410 holds processor module 200 securely in place within the garment, providing greater stability and gives the wearer the ability to control the feedback via switch 470.

The waistband is typically the most stable region within any sort of apparel, but more specifically in lower body apparel. This area of the garment is the least affected by regular human motion as well as by any external stimulus. Thus, the waistband provides the ideal platform to host any sensors as well as other electro-mechanical components.

Waistbands are traditionally created with multiple layers of material which provides room for component integration as well as opportunity for encapsulation of electro-mechanical systems from both visual and tactile perspectives. In the same manner, it provides protection for the components (electronic or other) that may be contained within.

Waistbands fit snugly around the body (as opposed to other areas of traditional apparel) hence provide a good opportunity to incorporate sensors that needs to touch or be close to the body without forcing the wearer to use unnaturally fitting garments.

Waistbands are usually manufactured as a separate manufacturing step within the garment manufacturing process. This allows for the integration of various electro-mechanical components within the garment without disrupting multiple steps of the garment manufacturing by containing it within the waistband creation process.

The electro-mechanical system in the waistband may consist of multiple components. Various combinations of these options can be used for different applications. The options include but are not limited to; Flexible dock/pockets; Conductive/data paths and interconnects (textile circuitry); various sensors; various feedback actuators; various indicators (such as LED or OLED lighting); various user control mechanisms (such as switches). In one particular embodiment, the electro-mechanical system in the waistband 11 could consist of a flexible dock 410, conductive/data paths 14 and interconnections 450 and switch control mechanism 470. The components visible to the user would be the flexible dock 410 and outer layer of the switch 470. The rest of the components would be concealed within the waistband 11. The dock and conductive/data paths would be integrated and encapsulated within the garment as described previously and the switch could be encapsulated using one of the many encapsulation options. Once encapsulated this system could also be washed and maintained as regular apparel, without requiring any special treatment. Also the system would support the controlled stretch, holding power and seamless appearance of any other waistband. The waistband containing the electro-mechanical system could be fabricated by using any or all of the regular options used in a waistband, including gathered waistbands, plain waistbands and exposed waistbands.

A garment system as described can cater to various different activities (including long distance running). Other such activities include; swimming, cycling, rowing, walking, tennis, weight lifting, training for different sports, rehabilitation, physiotherapy, warehousing and logistics and such.

As described the garment is a pair of shorts. However, the garment may be a t-shirt, compression top, shorts, tights, compression shorts, leggings, pants, capris, camisoles.

The user can buy one or more garments 100 and processor module 200 (which can be used on multiple garments, the interface on all garments being the same). The user will download the mobile application to their smart phone. The user will connect the electronic module to the app and enter their personal variables to customize the feedback to their profile. The user will attach the module to the garment prior to starting the run. Optionally, user can connect the module to app to obtain feedback from the app and run as usual.

The smart garment system will detect the form and technique of the user during the activity and provide improvement feedback via the actuators (the user can customize the frequency and type of the feedback via the app or turn off feedback from the module as their preference). Optionally, the user can receive feedback in audio/visual form from the software app if it's connected to the module while the user is running (this might require a separate headset to receive audio feedback. This feedback may be customizable as above). The user may also request feedback via the control interface (switch 470) as provided on the garment. The system (algorithm) will learn some of the intrinsic and unique features of the user in order to adapt future feedback. The user can connect the module to the app 230 (if not done before) to transfer the run data to the app.

The user is able to review post-run analytics and historical data on the app 230. If the module is not connected to the app 230 after a particular run, it will retain the data until the connection is made subsequently (typically, the module will retain up to 50 hours of data, after which the first data will be overwritten). The user can leave the module 200 in the garment for washing and maintenance for future usage.

The user will charge the module as needed (typically, the battery can last for 50 hours of use), and for charging the module will need to be removed from the garment.

The user will wash and maintain the smart apparel the same as any regular apparel with or without the module embedded. The smart garment will have a functional lifetime similar to (or more than) that of a regular running garment of comparable format.

The system is built in to apparel that every runner normally wears, thus eliminating the need to invest in and carry an extra device on their body.

In all embodiments of the invention, the conductive and data communication paths are capable of meeting the data rate and sampling requirements of motion sensors as well as load and current requirements of haptic actuators, by which they are far superior to any alternative textile based data/conductive mechanisms.

The garment itself provides an interface for control to the user, which is unique and hitherto not available from any smart garment.

The unique connection interface between the (detachable) module and apparel is refined in such a way that it provides a stable connection for the electronic functionality while not compromising apparel utility factors of comfort, flexibility and washability (of the interconnections).

The electronics within the processor module 200 will typically enable the battery to last for up to 50 hours of use (8 weeks of typical running) in contrast to current wearable products which typically lasts <20 hours.

Example of the System in Use

SCENARIO: A recreational runner is on a training run with an embodiment of the system of the invention. The system comprises of a pair of shorts coupled with the detachable processor module 200, preferably in the waistband of the shorts. The runner will have previously entered their basic bio-physical information (such as age, weight, height) to the system via the software application 230 and the processor module 200 is attached to the garment via the interface connector 18. The system in this embodiment has seven sensors 12 and a three haptic actuators 16 integrated into the shorts. The sensors 12 are placed to detect the kinematic parameters required to monitor running form and technique and the actuators 16 are placed to deliver discernible feedback in key areas of the body that helps the wearer to distinguish the action needed by them.

The shorts are constructed as follows:
Base fabric: Polyester/Spandex or Nylon/Polyester/Spandex composite, Synthetic fibre
Construction: Fitted to the body, close fit, light compression or regular fit shorts Conductive mechanism: Twisted stretchable conductive yarn for sensors, pattern laid stainless steel yarn for actuators (to account for different load delivery)
Sensor encapsulation: moulded silicone
Actuator encapsulation: polyurethane tape+textile
Conductive path encapsulation: polyurethane tape+textile
Apparel electronic interface: flexible dock/pocket 410

FIG. 9 shows a logic flow used by the system to monitor stride length. The system would recognize when the runner starts the training run through accelerometry data from the sensors 12 and start polling the sensors 12 and analyzing the data. There are allowances built in to allow the relatively chaotic data from the swarm-up' and 'cool-down' periods to be filtered out, so that any unnecessary or premature feedback is not given to the runner. Once the system detects that the runner is in a natural running motion, the sensor data is imputed, step 302, and the systematic interpretation of sensor data starts.

The sensor data will be subject to a noise filtering algorithm at step 304, and subjected to digital signal processing (DSP). The sensors are polled at a set frequency, and the processed kinematic data will be normalized before the system decides that the input data is complete, step 306.

The derived kinematic data 308 will be inspected for parameters and optimal ranges determined by the biomechanical model. The allowances are stored in the firmware as a dynamic variable which will be fine-tuned or personalized to the individual runner over time through the analysis of trends and the runners' reaction to the feedback given by the system.

The real-time kinematic data will be inspected in conjunction with over-time data (the trend) to provide context 309. Upon inspection of data, the system will decide if the kinematic parameter is within optimal ranges or not in the current context—for example in FIG. 3 that the stride length is outside of a range allowance 310.

In the case of the kinematic parameter being out of an optimal range, the system will further decide if any feedback on the particular kinematic would be detrimental to the performance of the runner in the current context of all (holistic) kinematic data captured, for example will changing stride length affect other current kinematics negatively, step 312. The feedback component of the biomechanical model will dictate how to gauge the impact of changing kinematics on other biomechanical aspects.

The system will further check at step 314 if there is additional feedback currently in progress, or queued before delivering feedback on the out of range kinematic, as concurrent or sequential feedback maybe less effective. Depending on the importance the system attaches to the kinematic variable and the feedback at step 316, the data will either be stored for future contextual analysis or put in a queue.

When a kinematic variable is due for feedback, the actuator management system will take over and deliver the appropriate haptic feedback at step 318; at the correct location for the kinematic, in the correct duration, intensity and pattern (i.e. a simple 'haptic language').

The runner (wearer of the system) can elect to react or not react to the haptic feedback given, but given the runner's objective and the intuitive nature of the feedback it is very much likely that they will adjust and adapt to the given feedback.

The system will recursively continue to capture, and inspect kinematic data and provide relevant feedback, until the running activity ceases.

The runner (wearer of the system) will be able to adjust the amount and type of feedback (i.e. which kinematic variables will take priority) through the software application.

The stored data 320 after each 'run' (as recognized automatically by the system itself) can be transmitted to the software application for further analysis, graphical representation and the formulation of a score for each of the kinematic categories—indicating how close the particular 'run' has fared against the biomechanical standard. An overall 'run score' would also be calculated from the weighted average of the scores for kinematic categories.

As an alternative, in situations in which the runner carries the portable electronic device 220 with them on the run, the system will transfer the particular kinematic information (via Bluetooth wireless transmission for example) to the software application where it will be indicated as a message/indicator on the screen for a predetermined duration as well as a vibration from the device's vibrator (if enabled).

Other variations and modifications will be apparent to the skilled person. Such variations and modifications may involve equivalent and other features that are already known and which may be used instead of, or in addition to, features described herein. Features that are described in the context of separate embodiments may be provided in combination in a single embodiment. Conversely, features that are described in the context of a single embodiment may also be provided separately or in any suitable sub-combination.

It should be noted that the term "comprising" does not exclude other elements or steps, the term "a" or "an" does not exclude a plurality, a single feature may fulfil the functions of several features recited in the claims and reference signs in the claims shall not be construed as limiting the scope of the claims. It should also be noted that the Figures are not necessarily to scale; emphasis instead generally being placed upon illustrating the principles of the present invention.

The invention claimed is:

1. A garment comprising:
   at least one textile panel;
   a waistband coupled to the at least one textile panel, wherein said waistband comprises a flexible interface connector provided with at least two flexible conductive connective regions;
   at least one data transmission path embedded in said at least one textile panel, the at least one data transmission path being connected to said conductive connective regions of said interface connector and at least one sensor for detecting at least one parameter relating to motion of the garment, said at least one sensor being connected to said interface connector by the at least one embedded data transmission path, wherein said at least one sensor is encapsulated or integrated within said at least one textile panel;
   wherein when the garment is secured against a user's body by the waistband and when the at least two flexible conductive connective regions of the garment are connected to a processing unit of a system, the system monitors the technique of the user undertaking a physical activity.

2. A garment according to claim 1 wherein a further one of said at least one sensor is located within said waistband.

3. A garment according to claim 1 in which the garment additionally comprises at least one actuator embedded in the garment for providing a feedback response to the user.

4. A garment according to claim 3 wherein the at least one actuator is one or more of a haptic actuator, thermal actuator, peltier tiles, TENS actuator, or electro-active polymer or micro-piezo actuator.

5. A garment according to claim 3 wherein the at least one actuator is located in said waistband.

6. A garment according to claim 3 wherein the at least one actuator is connected to said interface connector via at least one data transmission path.

7. A garment according to claim 1 further comprising a control switch connected to said interface connector via at least one data transmission path.

8. A system for monitoring the technique of a user undertaking a physical activity, the system comprising:
a garment having:
at least one textile panel;
a waistband coupled to the at least one textile panel, for securing the garment against a part of the user's body, wherein said waistband comprises a flexible interface connector provided with at least two flexible conductive connective regions suitable for connecting to a processing unit of a system for monitoring the technique of the user undertaking a physical activity, said garment further comprising:
at least one data transmission path embedded in said at least one textile panel, the at least one data transmission path being connected to said conductive connective regions of said interface connector and at least one sensor for detecting at least one parameter relating to motion of the user while the user is engaged in physical activity, said at least one sensor being connected to said interface connector by the at least one data transmission path, wherein said at least one sensor is encapsulated or integrated within said at least one textile panel, and worn by the user;
a processing unit configured to receive information about the at least one parameter from the at least one sensor, to compare the at least one parameter with at least one aspect of a biomechanical model of the physical activity, and to determine if a feedback response is required; and
at least one actuator embedded in or carried by the garment for providing the feedback response to the user during the physical activity.

9. A system according to claim 8 wherein the biomechanical model comprises a database of kinematic parameters and optimal ranges for each of the parameters, and wherein the model is generated by an analysis of the motion of a plurality of individuals.

10. A system according to claim 9 wherein the plurality of individuals comprises a cohort of high performance individuals and a cohort of low performance individuals.

11. A system according to claim 8 in which the physical activity is running.

12. A system according to claim 8 in which the at least one actuator is embedded in the garment.

13. A system according to claim 8 wherein the at least one actuator is one or more of a haptic actuator, thermal actuator, peltier tiles, TENS actuator, electro-active polymer or micro-piezo actuator.

14. A system comprising the garment according to claim 1 and a processing unit, wherein the flexible interface connector comprises a docking pocket for securely receiving said processing unit, wherein said system monitors the technique of the user undertaking the physical activity.

15. A system according to claim 14 wherein said docking pocket is provided in the waistband of said garment.

16. A garment according to claim 1 wherein the flexible conductive connective regions are formed from one or more of: flexible metal foils, conductive fabric patches, a conductive embroidery patch, conductive ink print, silver print, conductive silicone, conductive glue, or polymer patches.

17. A garment according to claim 3 wherein said at least one actuator is formed by printing directly onto textile material of the garment.

18. A system comprising the garment according to claim 1 and a processing unit, wherein the processing unit is connected with the at least two flexible conductive connective regions of the garment.

* * * * *